US007579507B2

United States Patent
Kasai et al.

(12) United States Patent
(10) Patent No.: US 7,579,507 B2
(45) Date of Patent: Aug. 25, 2009

(54) POLYMORPHIC CRYSTAL OF 4'-{2-[ (1S, 2R)—2- HYDROXY-2- (4-HYDROXYPHENYL)- 1-METHYLETHYLAMINO]ETHOXY} - 3 - ISOPROPYL-3', 5' -DIMETHYLBIPHENYL- 4 - CARBOXYLIC ACID HYDROCHLORIDE

(75) Inventors: Kiyoshi Kasai, Niigata (JP); Takehiro Ishikawa, Nagano (JP); Tetsuji Ozawa, Niigata (JP); Koji Kamata, Niigata (JP); Ritsu Suzuki, Nagano (JP); Hideki Takeuchi, Nagano (JP)

(73) Assignee: Kissei Pharmaceutical Co., Ltd., Matsumoto-Shi (JP)

( * ) Notice: Subject to any disclaimer, the term of this patent is extended or adjusted under 35 U.S.C. 154(b) by 0 days.

(21) Appl. No.: 11/871,710

(22) Filed: Oct. 12, 2007

(65) Prior Publication Data
US 2008/0076826 A1    Mar. 27, 2008

Related U.S. Application Data

(63) Continuation-in-part of application No. PCT/JP2006/308267, filed on Apr. 20, 2006.

(30) Foreign Application Priority Data
Apr. 22, 2005  (JP) .............................. 2005-125289
Oct. 13, 2006  (JP) .............................. 2006-279978

(51) Int. Cl.
*C07C 217/14*    (2006.01)

(52) U.S. Cl. ...................... 568/585; 568/586; 562/405; 562/442; 514/567; 514/646

(58) Field of Classification Search ...................... None
See application file for complete search history.

(56) References Cited

U.S. PATENT DOCUMENTS 7,417,169  B2    8/2008    Kobayashi et al.
2006/0128807  A1    6/2006    Kobayashi

FOREIGN PATENT DOCUMENTS

| CA | 2541894 | * | 5/2005 |
| WO | 2004 072016 A1 | | 8/2004 |
| WO | 2006 022237 A1 | | 3/2006 |

* cited by examiner

*Primary Examiner*—Daniel M Sullivan
*Assistant Examiner*—Sudhakar Katakam
(74) *Attorney, Agent, or Firm*—Westernman, Hattori, Daniels & Adrian, LLP.

(57) ABSTRACT

Crystals of a salt of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid. The α type, β type and γ type crystals produced by treating hydrochloride of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid with specified solvents, which can be discriminated by the characteristic diffraction peaks of powder X-ray diffractometry and the like.

3 Claims, 9 Drawing Sheets

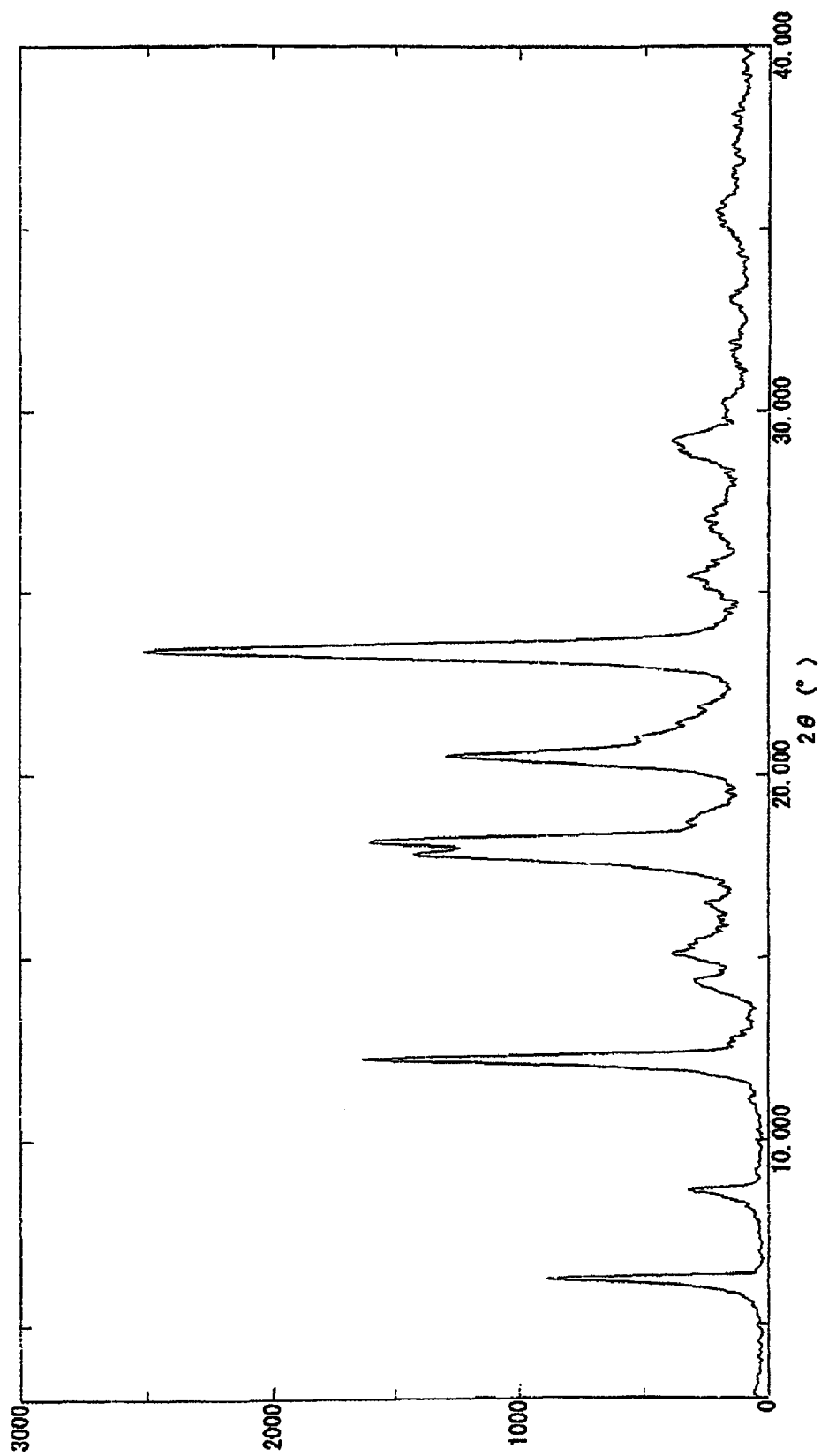

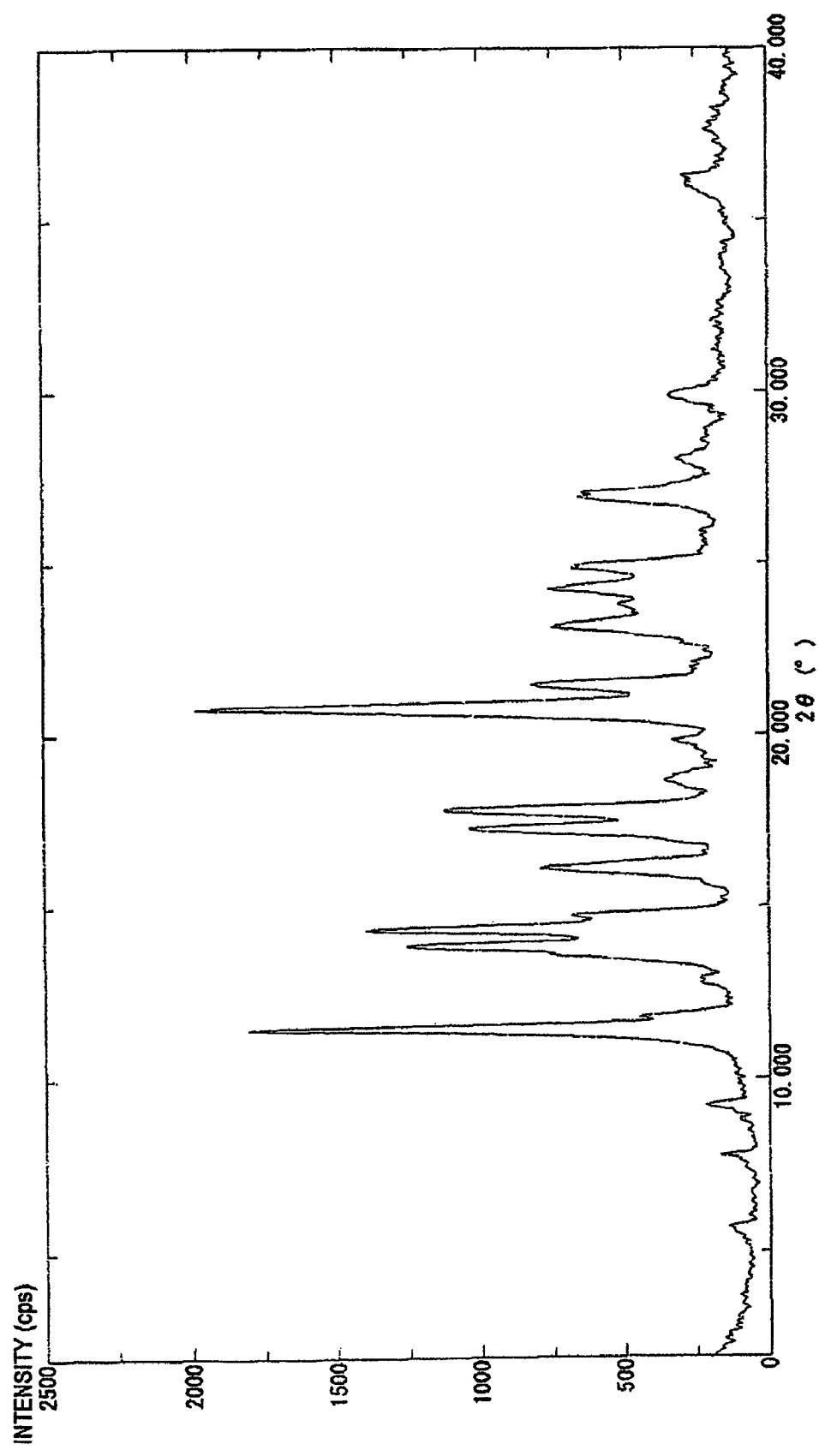

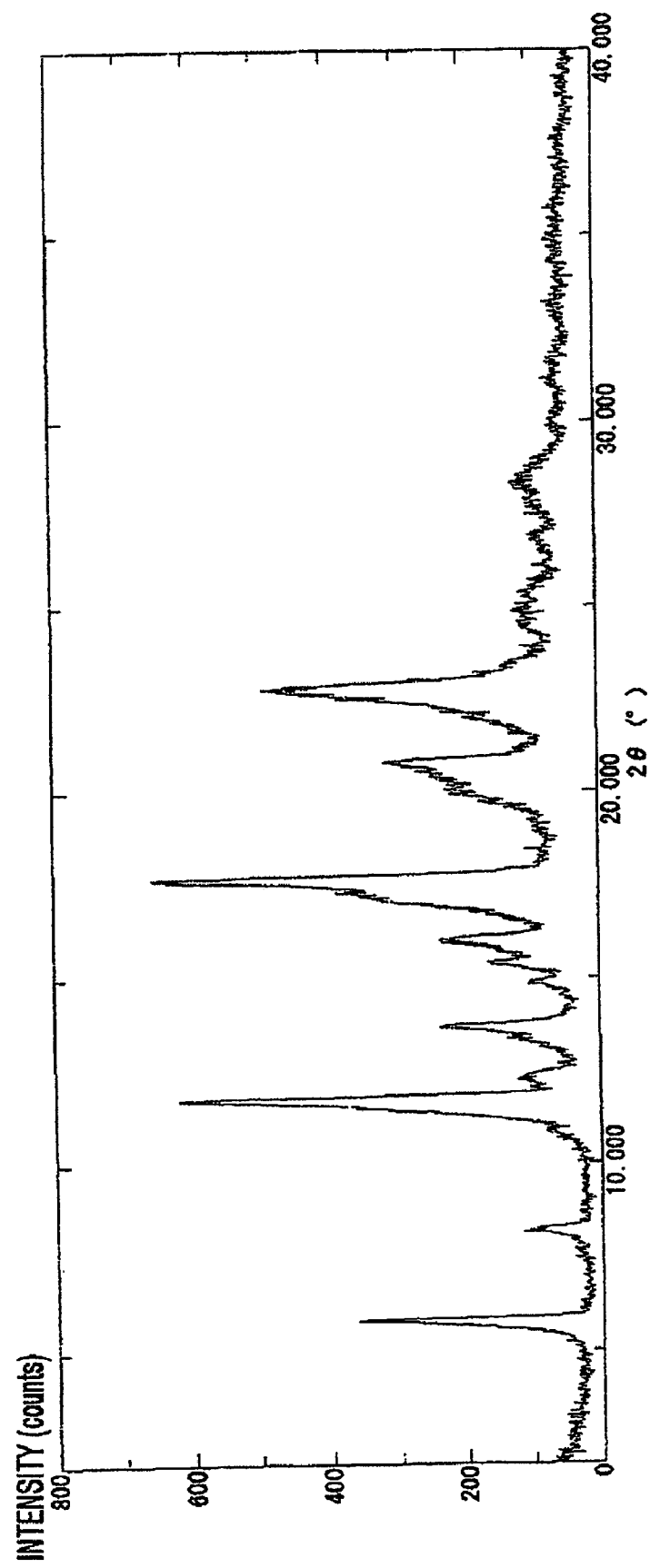
[Fig.3]

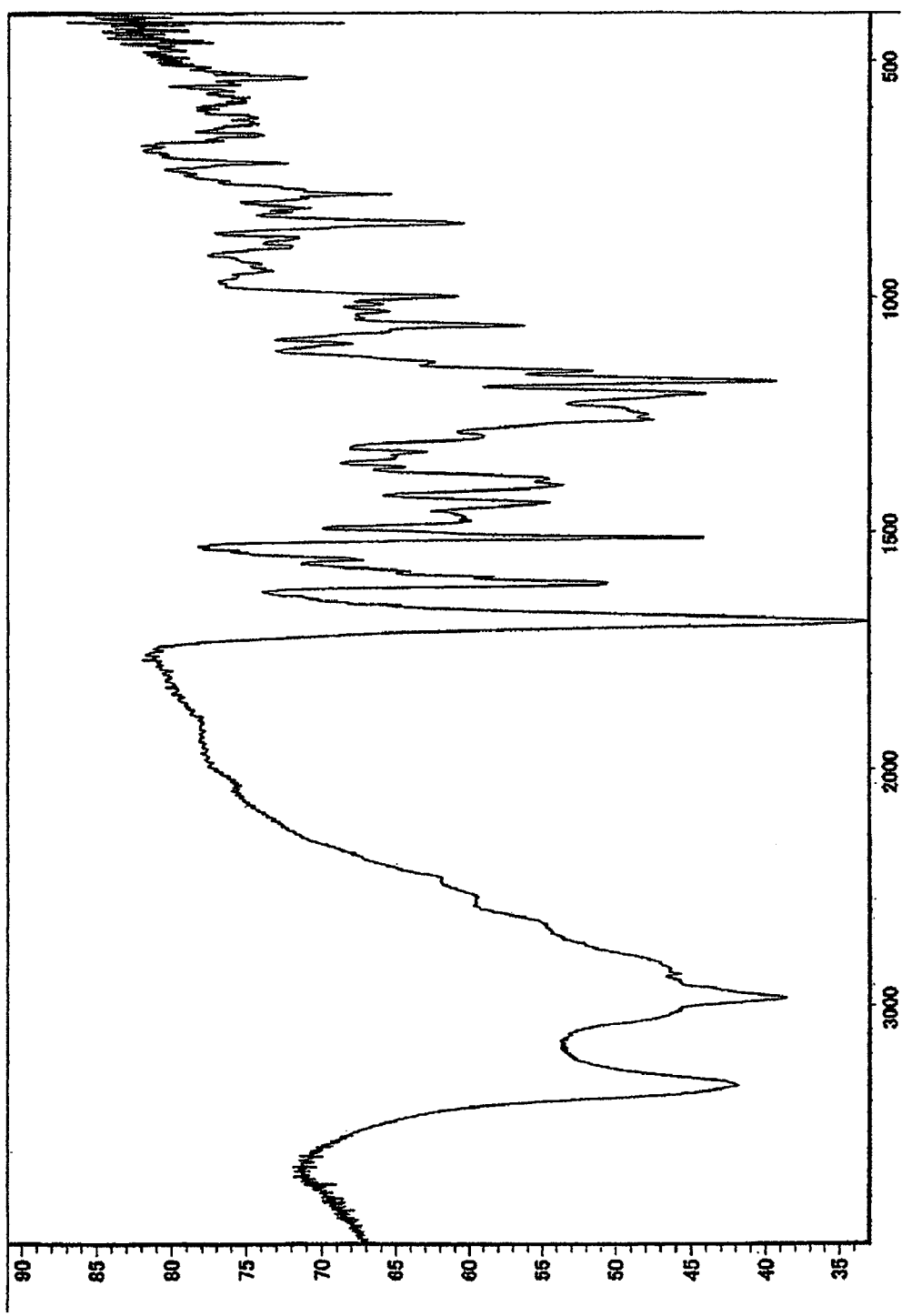

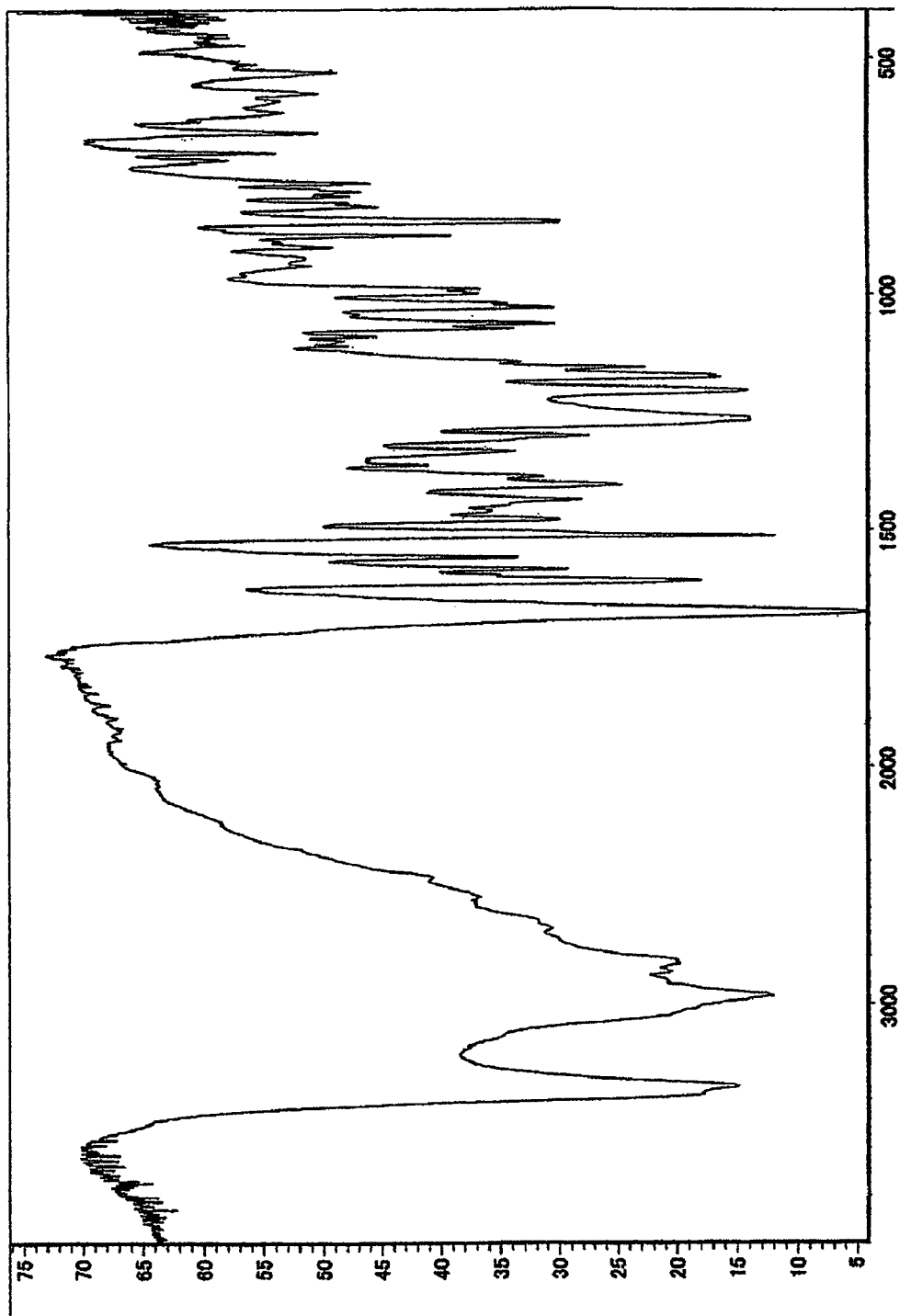
[Fig.5]

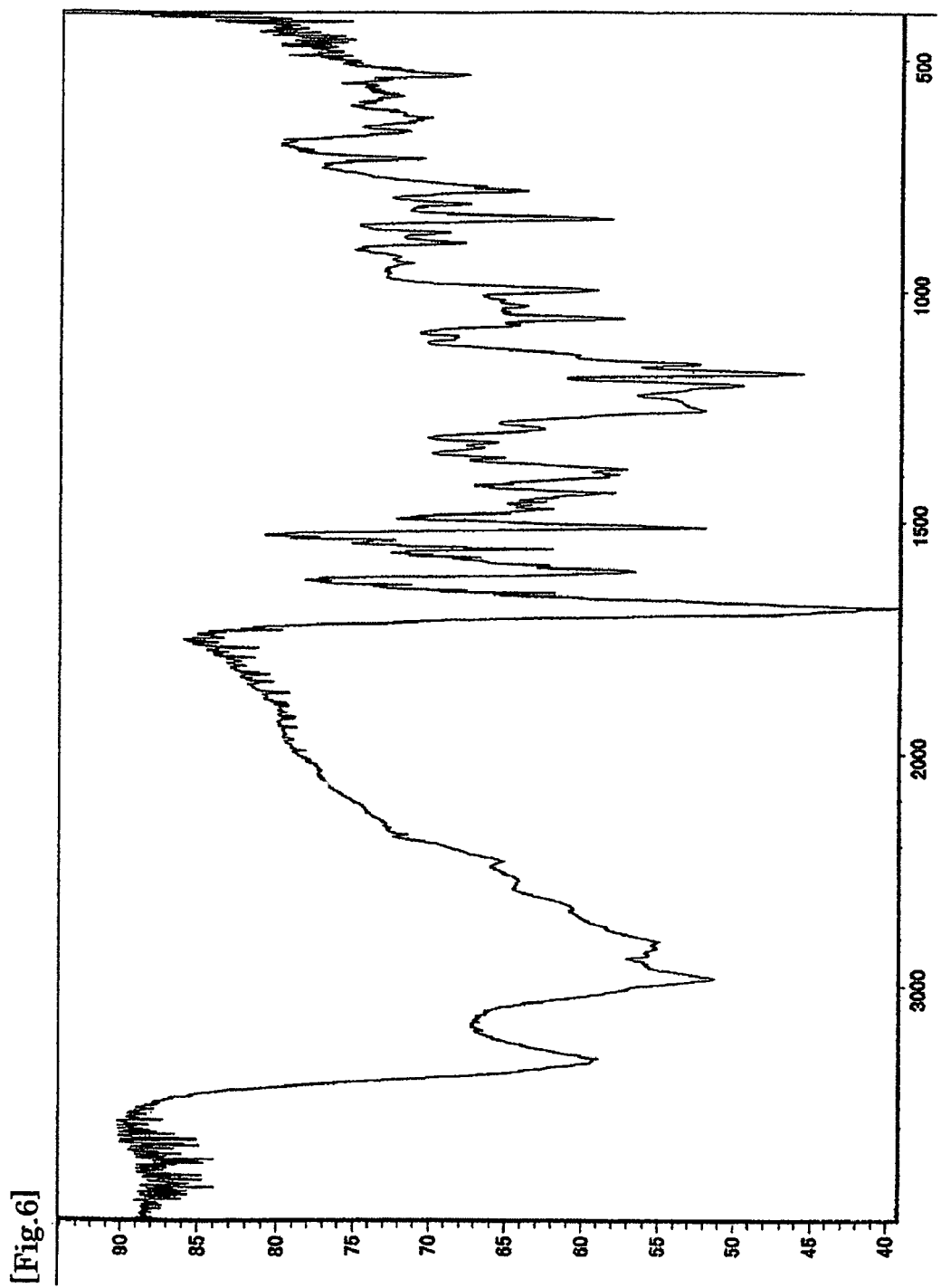
[Fig.6]

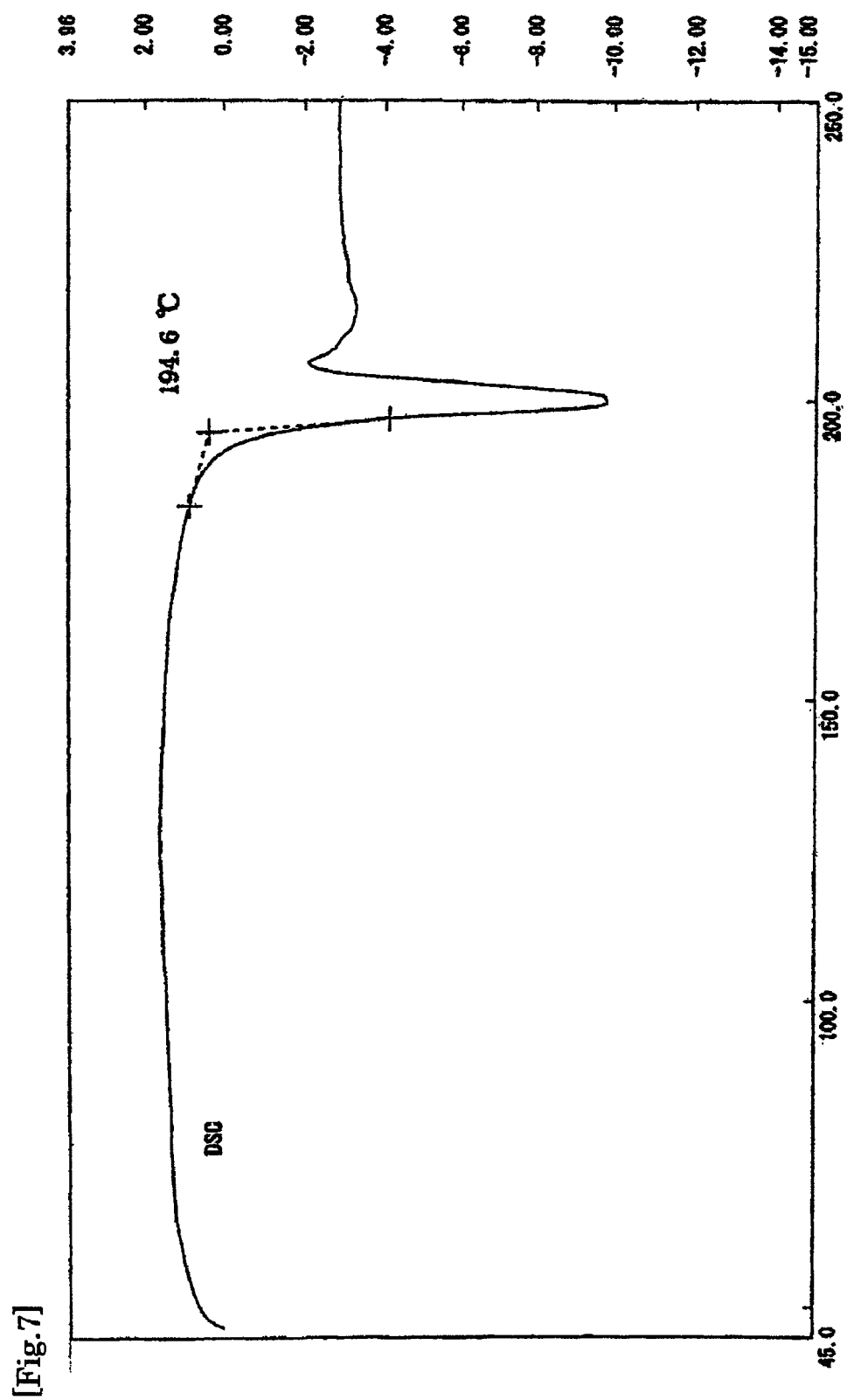
[Fig.7]

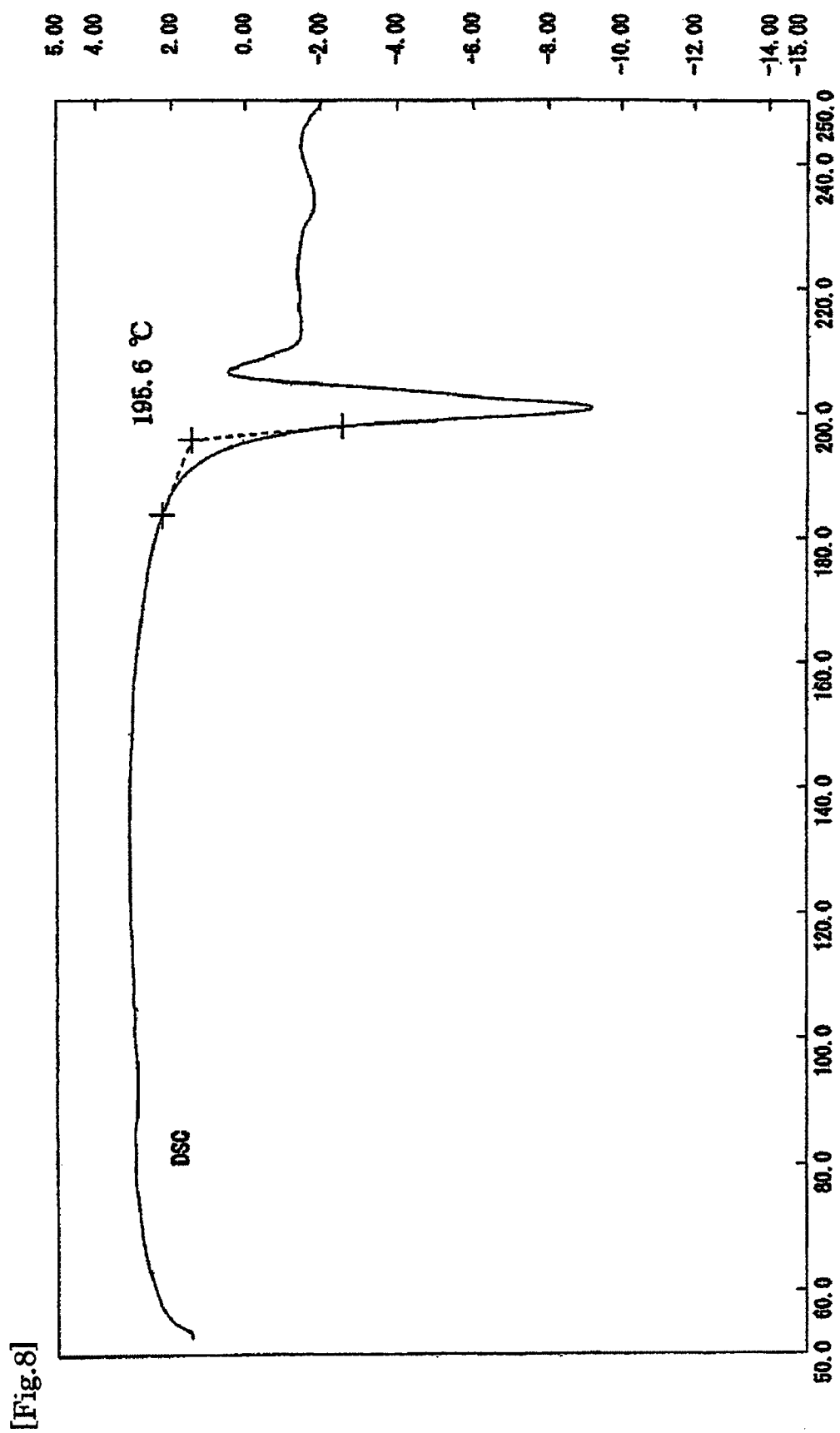
[Fig.8]

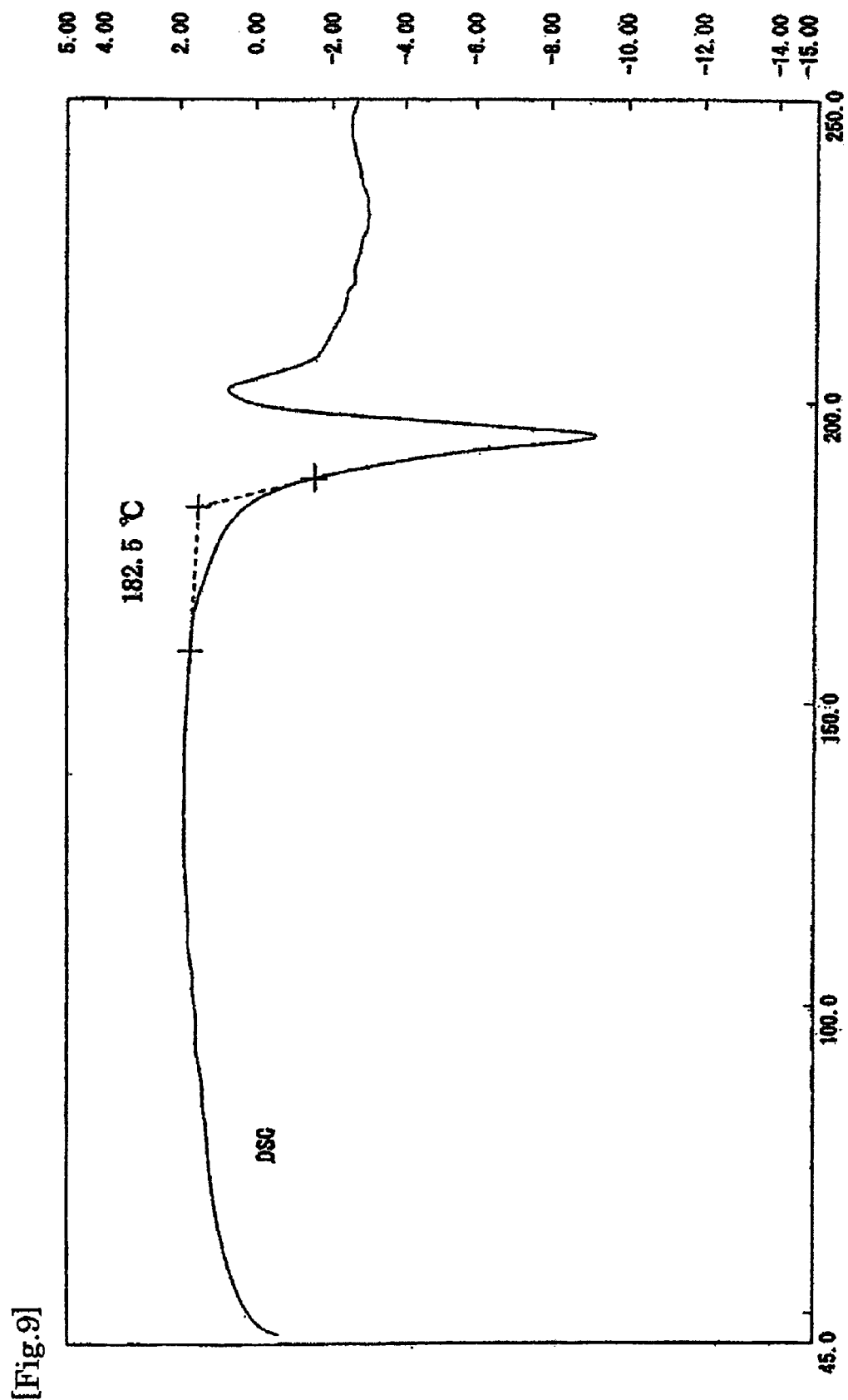
[Fig.9]

POLYMORPHIC CRYSTAL OF 4'-{2-[ (1S, 2R)—2- HYDROXY-2- (4-HYDROXYPHENYL)-1-METHYLETHYLAMINO]ETHOXY} - 3 - ISOPROPYL-3', 5' -DIMETHYLBIPHENYL- 4 - CARBOXYLIC ACID HYDROCHLORIDE

CROSS REFERENCES TO RELATED APPLICATIONS

This application is a Continuation-in-Part of prior International Application No. PCT/JP2006/308267, filed on Apr. 20, 2006, which claims benefit of Japanese patent application No. 125289/2005, filed Apr. 22, 2005, and this application claims benefit of Japanese patent application No. 279978/2006, filed Oct. 13, 2006, the entire contents thereof are hereby incorporated by reference.

FIELD OF THE INVENTION

This invention relates to the polymorphic crystal of 4'-{2-[(1S,2R)-2-2-hydroxy-2-(4-hydroxyphenyl)-1-methylethylamino]ethoxy}-3-isopropyl-3',5'-dimethylbiphenyl-4-carboxylic acid hydrochloride which has a $\beta_3$-adrenaline receptor stimulative action.

BACKGROUND OF THE INVENTION

4'-{2-[(1S,2R)-2-Hydroxy-2-(4-hydroxyphenyl)-1-methylethylamino]ethoxy}-3-isopropyl-3',5'-dimethylbiphenyl-4-carboxylic acid shows an excellent $\beta_3$-adrenaline receptor stimulative action, and this compound can be used as a treating or preventive agent for obesity, diabetes, hyperlipemia, depression, urinary disturbance, a disease caused by gallstone or biliary tract motor acceleration, a disease caused by digestive tract function acceleration and the like. Regarding any one of said compound and several salts thereof, merely the presence of amorphous solids is known but the presence of crystals is not known (cf. Patent Reference 1).

In general, an amorphous solid is hard to use as a medicinal bulk, because it has a problem regarding residual solvent, a problem regarding control of homogeneity of the content in making a pharmaceutical preparation, and further a problem regarding stability during its storage and the like. In addition, in general, a salt is superior to the free compound with respect to the in vivo absorbing ability, so that a salt is desirable as a medicinal bulk.

Thus, a crystal of a salt of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid is in demand.

Patent Reference 1: International Publication WO2004/072016 and related U.S. Patent Publication No. US2006/0128807, which are hereby incorporated by reference.

SUMMARY OF THE INVENTION

The invention aims at providing crystals of a salt of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid (sometimes, to be referred to as "biphenylcarboxylic acid compound" hereinafter).

In order to solve the aforementioned problems, the present inventors have conducted extensive studies on the crystallization of a salt of the biphenylcarboxylic acid compound and, as a result, found that three types of crystal forms can be obtained by treating hydrochloride of the biphenylcarboxylic acid compound in combination with specified solvents, thereby accomplishing the present invention.

All of the crystals concerned in the invention, particularly the α type, β type and γ type crystals, have no problems regarding residual solvents and are excellent in the stability during storage.

BRIEF DESCRIPTION OF THE DRAWINGS

By way of example and to make the description more clear, reference is made to the accompanying drawing in which:

FIG. 1 is a powder X-ray diffraction diagram of the α type crystals obtained in Example 2. The axis of ordinate shows intensity of X-rays (CPS), and the axis of abscissa shows angle of diffraction (2θ).

FIG. 2 is a powder X-ray diffraction diagram of the β type crystals obtained in Example 3. The axis of ordinate shows intensity of X-rays (CPS), and the axis of abscissa shows angle of diffraction (2θ).

FIG. 3 is a powder X-ray diffraction diagram of the γ type crystals obtained in Example 4. The axis of ordinate shows intensity of X-rays (CPS), and the axis of abscissa shows angle of diffraction (2θ).

FIG. 4 is an IR spectrum of the α type crystal obtained in Example 2. The axis of ordinate shows intensity (%), and the axis of abscissa shows wave number ($cm^{-1}$).

FIG. 5 is an IR spectrum of the β type crystal obtained in Example 3. The axis of ordinate shows intensity (%), and the axis of abscissa shows wave number ($cm^{-1}$).

FIG. 6 is an IR spectrum of the γ type crystal obtained in Example 4. The axis of ordinate shows intensity (%), and the axis of abscissa shows wave number ($cm^{-1}$).

FIG. 7 is a DSC curve of the α type crystal obtained in Example 2. The axis of ordinate shows quantity of heat (mW) and the axis of abscissa shows temperature.

FIG. 8 is a DSC curve of the β type crystal obtained in Example 3. The axis of ordinate shows quantity of heat (mW) and the axis of abscissa shows temperature.

FIG. 9 is a DSC curve of the γ type crystal obtained in Example 4. The axis of ordinate shows quantity of heat (mW), and the axis of abscissa shows temperature.

DETAILED DESCRIPTION OF THE INVENTION

The α type, β type and γ type crystals of the biphenylcarboxylic acid compound hydrochloride can be produced respectively by the methods described in the following. In this connection, the biphenylcarboxylic acid compound or its hydrochloride prepared by the methods described in Example 4 or Example 14 of the Patent Reference 1 can be used for the production of each crystal.

The α type crystals can be produced by dissolving the biphenylcarboxylic acid compound hydrochloride in a good solvent selected from water; methanol, ethanol or the like alcohol solvent; N,N-dimethylformamide (DMF) or the like amide solvent; dimethyl sulfoxide (DMSO); acetonitrile and the like, subsequently mixing this with a poor solvent selected from acetone, methyl ethyl ketone or the like ketone solvent; t-butyl methyl ether, tetrahydrofuran or the like ether solvent; toluene or the like aromatic hydrocarbon solvent; a formic acid ester, methyl acetate or ethyl acetate and the like, and then collecting the precipitated crystals. The good solvent solution of the biphenylcarboxylic acid compound hydrochloride can be prepared either by dissolving the free biphenylcarboxylic acid compound in a good solvent and then adding hydrochloric acid or hydrogen chloride gas thereto, or by dissolving the free biphenylcarboxylic acid compound in a good solvent containing hydrogen chloride. In addition, according to the aforementioned production method, there is a case in which a mixture of the α type crystals with a solvate thereof is precipitated at the time of the precipitation of the crystals. In such a case, pure α type crystals can be produced by heating this mixture under ordinary pressure or a reduced pressure.

The β type crystals can be produced by carrying out the treatment in the same manner as in the production method of α type crystals, except that isopropyl acetate or propyl acetate is used as the poor solvent in the production method of α type crystals, and heating the thus formed crystals of the solvate of isopropyl acetate or propyl acetate under ordinary pressure or a reduced pressure.

The γ type crystals can be produced in accordance with the production method of α type crystals, by using 2-propanol or ethanol as the good solvent and using n-heptane as the poor solvent.

A single solvent may be used or a mixed solvent as a combination of two or more solvents may be used in the good solvent and poor solvent to be used in the production of respective crystal forms. In addition, it is preferable to use the poor solvent in an amount of approximately 4 volumes of the good solvent.

Purity of the crystals produced by the method described in the above can be improved by repeating the production method. In that case, when a seed crystal is inoculated, the yield is improved and crystals having uniform particle diameter and particle size distribution can be obtained.

As shown in the powder X-ray diffraction charts of FIGS. 1 to 3, respective α type, β type and γ type crystals of the biphenylcarboxylic acid compound hydrochloride obtained in this manner can be discriminated from one another based on the characteristic diffraction peaks shown in the following.

As shown in FIG. 1, diffraction pattern of the α type crystals by the powder X-ray diffractometry has characteristic peaks at diffraction angles (2θ) of 6.22, 8.60, 12.2, 15.4, 17.8, 18.2, 18.8, 20.5 and 23.4°.

As shown in FIG. 2, diffraction pattern of the β type crystals by the powder X-ray diffractometry has characteristic peaks at diffraction angles (2θ) of 9.2, 11.4, 13.8, 14.3, 16.1, 17.2, 17.8, 20.7, 21.4, 22.0, 23.2, 24.3, 24.9, 26.9, 28.0 and 29.9°.

As shown in FIG. 3, diffraction pattern of the γ type crystals by the powder X-ray diffractometry has characteristic peaks at diffraction angles (2θ) of 5.78, 8.20, 11.7, 13.7, 17.1, 17.6, 18.8, 20.7 and 22.7°.

In this connection, the 2θ value of diffraction pattern by the powder X-ray diffractometry may deviate in some cases by a factor of about 0.5° depending on the sample conditions and measuring conditions. In addition, due to the properties of data, a total diffraction pattern of the powder X-ray diffractometry is important for the identification of crystals.

In addition, each polymorphic crystal can also be discriminated based on the respective data of infrared absorption (IR) spectrum or differential scanning calorimetry (DSC). The IR spectra are shown in FIGS. 4 to 6, and the DSC in FIGS. 7 to 9.

The α type, β type and γ type crystals of the biphenylcarboxylic acid compound hydrochloride do not cause mutual changes in the crystal forms during their preservation under usual conditions (25° C., 60% relative humidity) or during pressurization, pulverization and the like medicine preparation steps. In addition, since they are chemically stable and also excellent in fluidity and the content homogeneity in the steps of making a pharmaceutical preparation, they are suited as medicinal bulks.

The crystals concerned in the invention can be used as the active ingredient of a medicament as a single crystal form or as a combination of two or more crystal forms. That is, a pharmaceutical composition can be produced by optionally mixing said crystals with pharmaceutical additive agents selected from an excipient, a disintegrating agent, a binder, a lubricant, a diluent, a buffer agent, a tonicity agent, an antiseptic, a moistening agent, an emulsifying agent, a dispersing agent, a stabilizing agent, a solubilizing agent and the like.

The pharmaceutical composition concerned in the invention can be administered orally or parenterally, for example by preparing it into powders, granules, fine granules, dry syrups, tablets, capsules, injections, solutions, ointments, suppositories, patches and the like dosage forms. It is desirable to make a pharmaceutical preparation in such a manner that the biphenylcarboxylic acid compound hydrochloride is administered within the range of from about 0.01 mg to about 100 mg per day per adult in the case of oral administration or within the range of from about 0.003 mg to about 30 mg per day per adult in the case of parenteral administration.

EXAMPLES

The contents of the invention are described in the following further in detail using Examples and test examples, the invention is not limited thereto.

In this connection, respective data on the powder X-ray diffraction, IR spectrum and DSC were measured by the following means.

Powder X-ray diffraction: An X-ray diffractometer RINT 2100 manufactured by Rigaku Corporation (measuring conditions; CuK α rays, 40 kV in X-ray tube voltage, 40 mA in X-ray tube current)

IR: Nicolet AVATAR 320

Measured by FT-IR (resolution: 2, integrating frequency: 4) in accordance with the potassium chloride tablet method.

Differential scanning calorimetry (DSC): Rigaku thermal analyzer ThermoPlus input compensation type TG-DSC (TG-8110)

Authentic sample: aluminum oxide
Temperature rising: 10° C./min
Upper limit temperature: 260° C.
Lower limit temperature: 30° C.
Atmosphere: air
Sample pan: aluminum
Sample amount: 4 to 7 mg Example 1

α type crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride 4'-{2-[(1S,2R)-2-Hydroxy-2-(4-hydroxyphenyl)-1-methylethylamino]ethoxy}-3-isopropyl-3',5'-dimethylbiphenyl-4-carboxylic acid (2.00 g) was suspended in a mixed solvent of ethanol (4.0 ml) and acetonitrile (6.0 ml), and then 25 (w/w) % hydrogen chloride-ethanol solution (0.642 g) was added thereto at room temperature under stirring.

After confirming its dissolution by stirring at room temperature for 30 minutes, the stirring was further continued for 1 hour. After confirming the suspension, acetonitrile (16 ml) was added thereto.

After stirring at room temperature for 2 hours or more, this was cooled on ice and stirred for 1 hour. The suspension was filtered, and the crystals were washed twice with acetonitrile (4.0 ml) to obtain wet crystals. By drying at room temperature under a reduced pressure, the title crystals (2.00 g) were obtained.

Example 2

α type crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride 4'-{2-[(1S,2R)-2-Hydroxy-2-(4-hydroxyphenyl)-1-methylethylamino]ethoxy}-3-isopropyl-3',5'-dimethylbiphenyl-4-carboxylic acid hydrochloride (20 g) was suspended in a mixed solvent of ethanol (36 ml) and methyl acetate (50 ml), and then dissolved therein by heating under stirring.

By cooling down to 40° C., insoluble matter in the dissolved material was removed, the container was washed with a mixed solvent of ethanol (4 ml) and methyl acetate (10 ml) which had been heated in advance, and then filtration was carried out.

The filtrate was mixed with ethyl acetate (40 ml) at 40° C. and stirred until precipitation of crystals was confirmed. After adding methyl acetate (140 ml), this was stirred at 45° C. for 1 hour, and then methyl acetate (120 ml) was further added thereto.

This was cooled down to room temperature, stirred for a while and then further cooled on ice and stirred for 1 hour. The suspension was filtered, and the crystals were washed with acetonitrile (40 ml) to obtain wet crystals. By drying at 70° C. under a reduced pressure until the solvent was almost completely evaporated, the title crystals (18.1 g) were obtained.

Powder X-ray diffraction (2θ): 6.22, 8.60, 12.2, 15.4, 17.8, 18.2, 18.8, 20.5, 23.4.

Example 3

β type crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride 4'-{2-[(1S,2R)-2-Hydroxy-2-(4-hydroxyphenyl)-1-methylethylamino]ethoxy}-3-isopropyl-3',5'-dimethylbiphenyl-4-carboxylic acid hydrochloride (5.52 g) was suspended in isopropyl acetate (17 ml), mixed with 1-propanol (11 ml) at room temperature under stirring and then dissolved therein by heating at 90° C.

This was cooled down to 60° C. to remove insoluble matter in the dissolved material, washed with a mixed solvent of 1-propanol (2.0 ml) and isopropyl acetate (3.0 ml) which had been heated to 60° C. in advance, and then filtered.

After stirring at 50° C. until precipitation of crystals was confirmed, isopropyl acetate (22 ml) was added dropwise thereto at the same temperature.

The filtrate was cooled down to room temperature, stirred by adding isopropyl acetate (11 ml) and then further cooled on ice and stirred. The suspension was filtered, and the crystals were washed with isopropylacetate (11 ml) to obtain wet crystals. By drying at 90° C. under a reduced pressure until the solvent was almost completely evaporated, the title crystals (5.26 g) were obtained.

Powder X-ray diffraction (2θ): 9.2, 11.4, 13.8, 14.3, 16.1, 17.2, 17.8, 20.7, 21.4, 22.0, 23.2, 24.3, 24.9, 26.9, 28.0, 29.9.

Example 4

γ type crystal of 4'-{2-[(1S,2R)-2-hydroxy-2-(4-hydroxyphenyl)-1-methylethylamino]ethoxy}-3-isopropyl-3',5'-dimethylbiphenylcarboxylic acid hydrochloride 4'-{2-[(1S,2R)-2-Hydroxy-2-(4-hydroxyphenyl)-1-methylethylamino]ethoxy}-3-isopropyl-3',5'-dimethylbiphenyl-4-carboxylic acid hydrochloride (5.00 g) was suspended in ethanol (7.5 ml) and then dissolved therein by heating under stirring.

By cooling down to 60° C., insoluble matter in the dissolved material was removed, and the filtrate was further mixed with n-heptane (3.0 ml) at 40° C. and then, after confirming precipitation of crystals, further mixed with n-heptane (2.0 ml) and stirred.

While stirring, n-heptane (50 ml) was added dropwise thereto at 40° C. After cooling to room temperature under stirring, it was cooled on ice and stirred. The suspension was filtered, and the crystals were washed with n-heptane (5 ml) to obtain wet crystals. They were dried at 40° C. for 6 hours under a reduced pressure and further at 70° C. under a reduced pressure until the solvent was evaporated, thereby obtaining the title crystals (4.91 g).

Powder X-ray diffraction (2θ): 5.78, 8.20, 11.7, 13.7, 17.1, 17.6, 18.8, 20.7, 22.7.

Test Example 1

Solid Stability

Each of (1) amorphous biphenylcarboxylic acid hydrochloride (purity: 97.22%), (2) α type crystal of biphenylcarboxylic acid hydrochloride (purity: 99.56%) and (3) β type crystal of biphenylcarboxylic acid hydrochloride (purity: 99.84%) was stored at 60° C. and at a relative humidity of 75% for 5 days. Purities after the storage were (1) 94.99%, (2) 99.55% and (3) 99.65%, respectively. Accordingly, both of the α type crystal and β type crystal of biphenylcarboxylic acid hydrochloride are possessed of the storage stability superior to that of the amorphous compound.

Test Example 2

Solid Stability

Each of (A) the α type crystal of biphenylcarboxylic acid hydrochloride (purity 99.8%) and (B) the γ type crystal of biphenylcarboxylic acid hydrochloride (purity 99.8%) were stored (1) at 40° C. for 8 weeks, (2) at 60° C. for 8 weeks, (3) at 40° C. and at a relative humidity of 75% for 8 weeks and (4) at 40° C. and at a relative humidity of 90% for 8 weeks. Purities of (A) the α type crystal after the storage were (1) 99.79%, (2) 99.78%, (3) 99.58% and (4) 99.51%, respectively. Purities of (B) the γ type crystal after the storage were (1) 99.82%, (2) 99.88%, (3) 99.87% and (4) 98.20%, respectively. Accordingly, both of the α type crystal and the γ type crystal of biphenylcarboxylic acid hydrochloride are possessed of excellent storage stability.

The crystals according to the present invention have excellent storage stability and are excellent in terms of fluidity and handling, so that they are suited for making pharmaceutical preparations.

What is claimed is:

1. A crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride wherein its diffraction pattern by the powder X-ray diffractometry has characteristic peaks at diffraction angles (2θ) of 6.22, 8.60, 12.2, 15.4, 17.8, 18.2, 18.8, 20.5 and 23.4°.

2. A crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride wherein its diffraction pattern by the powder X-ray diffractometry has characteristic peaks at diffraction angles (2θ) of 9.2, 11.4, 13.8, 14.3, 16.1, 17.2, 17.8, 20.7, 21.4, 22.0, 23.2, 24.3, 24.9, 26.9, 28.0 and 29.9°.

3. A crystal of 4'-{2-[(1S,2R)-2-hydroxy-2-(4-hydroxyphenyl)-1-methylethylamino]ethoxy}-3-isopropyl-3',5'-dimethylbiphenyl-4-carboxylic acid hydrochloride wherein its diffraction pattern by the powder X-ray diffractometry has characteristic peaks at diffraction angles (2θ) of 5.78, 8.20, 11.7, 13.7, 17.1, 17.6, 18.8, 20.7 and 22.7°.

* * * * *